United States Patent [19]

Morisawa et al.

[11] 3,935,311
[45] Jan. 27, 1975

[54] SUBSTITUTE PYRIDINOL-CONTAINING COMPOSITIONS AND METHODS FOR THE TREATMENT OF COCCIDIOSIS

[75] Inventors: Yasuhiro Morisawa; Mitsuru Kataoka; Taiichiro Watanabe; Noritoshi Kitano; Toshiaki Matsuzawa, all of Tokyo, Japan

[73] Assignee: Sankyo Company Limited, Tokyo, Japan

[22] Filed: Sept. 26, 1974

[21] Appl. No.: 509,720

Related U.S. Application Data

[62] Division of Ser. No. 404,641, Oct. 9, 1973, Pat. No. 3,897,556.

[30] Foreign Application Priority Data

Oct. 20, 1972  Japan............................... 47-105090
Apr. 11, 1973  Japan............................... 48-41111

[52] U.S. Cl. ............................................... 424/200
[51] Int. Cl.² ........................................ A61K 31/675
[58] Field of Search ................. 424/200; 260/297 P

[56] References Cited
UNITED STATES PATENTS
3,743,648    7/1973    Rigterink.......................... 260/297 P

*Primary Examiner*—Frederick E. Waddell
*Attorney, Agent, or Firm*—Flynn & Frishauf

[57] ABSTRACT

A composition which comprises a pyridinol derivative of the formula

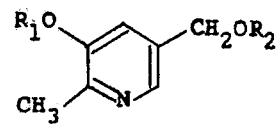

intimately dispersed in an inert edible carrier, wherein $R_1$ and $R_2$ may be the same or different and each represents a hydrogen atom; a lower alkyl group, an aralkyl group, an aliphatic, an aromatic or a heterocyclic acyl group; an alkoxycarbonyl group; an aralkoxycarbonyl group; an aryloxycarbonyl group; a N-substituted carbonyl group; a N-substituted thiocarbonyl group; a phosphono group; or a salt thereof.

The composition is a preventive and curative anticoccidial agent for poultry and domestic animals. Particularly, it shows a significant activity against chronic coccidiosis caused by *Eimeria acervulina*.

The composition is less toxic for animals, besides it has an advantage that it is also effective for coccidiosis caused by coccidia resistant to the known anticoccidial agents.

9 Claims, No Drawings

SUBSTITUTE PYRIDINOL-CONTAINING COMPOSITIONS AND METHODS FOR THE TREATMENT OF COCCIDIOSIS

This is a division of application Ser. No. 404,641, filed Oct. 9, 1973, now U.S. Pat. No. 3,897,556.

This invention relates to novel compositions and methods for the treatment and prevention of the poultry disease coccidiosis.

More particularly, it is concerned with novel compositions containing, as an active anticoccidial agent, certain pyridinol derivatives.

Coccidiosis is a common and widespread disease of poultry, especially chickens and turkeys, and domestic animals such as rabbits, goats, sheep, and cattles, which disease is caused by a kind of protozoa belonging to class Sporozoa, order Coccidia, family Eimeriidae.

Coccidiosis of Poultry and domestic animals is caused mainly by the protozoa belonging to genus Eimeria, which disease is classified to an acute type and a chronic one.

The former is caused by such species as $E.$ $tenella$ and $E.$ $necatrix$, and the characteristic feature of the disease is a copious bloody discharges from the ceca and small intestine of diseased poultry, which often die within a day or two.

The latter is caused by such species as $E.$ $acervulina$, $E.$ $maxima$, $E.$ $brunetti$, $E.$ $praecox$, $E.$ $hagani$, $E.$ $mitis$ and $E.$ $mivati$, and the characteristic feature of the disease is that the mortality of diseased poultry is rather few, whereas a poor weight gain, a reduced feed efficiency and a reduced efficiency of egg-production are commonly observed.

Infant rabbits as well as cattles, sheep and goats sometimes cause severe lesions by parasite Eimeria within there levers and intestines.

Oocysts of coccidia are excreted from an infected animal with feces, and spores having infectivity are produced within 24–48 hours under suitable conditions, which spores enter into a non-infected animal orally.

Oocysts grow at first asexually within the cells of the caecum or small intestine of the host animal, during which time the heaviest symptoms is observed. Then, they grow sexually and are excreted with the feces of the host animal and they exhibit an awful communicability.

The elimination or control of coccidiosis is, therefore, of paramount importance particularly in the poultry industry.

There have been proposed many preventive and curative methods for coccidiosis. One of them is a development in chemotherapeutic agents such as sulfa drugs, arsenic compounds, nitrofuran derivatives, nitrophenide, Nicarbazine, Zelane, pyrimidine derivatives (anti-thiamines), quinoline derivatives, guanidine derivatives, various antibiotics and so on.

But they have some defects; i.e. weak activity, narrow anti-protozoal spectrum, lack of security for animals or acquired resistance to the drugs by protozoa, respectively. Therefore, treatment with the hither-to-known anticoccidial agent is not satisfactory.

It is an object of this invention to provide novel compositions which are effective in treating and preventing coccidiosis.

Another object will become apparent from the following detailed description of this invention.

In accordance with this invention, it has now been found that the pyridinol derivatives having the formula

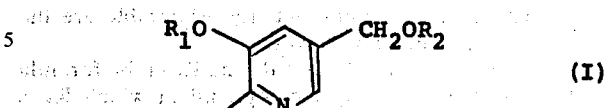

(I)

wherein $R_1$ and $R_2$ may be the same or different and each represents a hydrogen atom, a lower alkyl group; an aralkyl group, an aliphatic, an aromatic or a heterocyclic acyl group; an alkoxycarbonyl group; an aralkoxycarbonyl group; an aryloxycarbonyl group, a N-substituted carbamoyl group; a N-substituted thiocarbamoyl group; a phosphono group; or a salt therof posses significant anticoccidial activity, and may be used in the methods and compositions of this invention.

The above compounds and formula (I) have a preventative and curative anticoccidial activity against almost all species of genus Eimeria especially against $E.$ $acervulina$ to which no parctically effective anticoccidial agents have been known.

In addition, some of the above compounds have a growth promoting activity for poultry and domestic animals and their preventive application to non-infected animals brings the promotion of weight gain and the improvement of feed efficiency.

With regard to the above formula (I), the lower alkyl group may be preferably of 1 to 3 carbon atoms and exemplified by methyl, ethyl, n-propyl or isopropyl; the aralkyl group may be preferably benzyl group which may have halogen atom(s) such as chlorine in the benzene ring; the aliphatic acyl group may be a straight or branched alkanoyl or alkenoyl group of 2 to 18 carbon atoms in total, and the aliphatic acyl group may have substituents such as aryloxy group, and the aliphatic acyl group may be cycloalkanoyl group of 6 to 8 carbon atoms in total, and exemplified by acetyl, propionyl, butyryl, valeroyl, hexanoyl, octanoyl, palmitoyl, stearoyl, isobutyryl, isovaleroyl, pivaloyl, crotonoyl, phenoxyacetyl, 2-phenoxypropionyl or cyclohexanecarbonyl; the aromatic acyl group may be preferably a benzoyl or a naphthoyl group which may have 1 to 2 substituents such as lower alkyl-, alkoxy-, halogen-, nitro-, cyano-, carboxy- or acetylamino- in the aromatic ring and exemplified by benzoyl, naphthoyl, toluoyl, chlorobenzoyl, bromobenzoyl, methoxybenzoyl, nitrobenzoyl, cyanobenzoyl, carboxybenzoyl, acetylaminobenzoyl, 3,5-dimethylbenzoyl, 2,3-dimethoxybenzoyl or 3,4-dimethoxybenzoyl group; the heterocyclic acyl group is exemplified by 2-furoyl, 2-thermoyl, isonicotinoyl or nicotinoyl group; the alkoxycarbonyl group may have preferably 1 to 8 carbon atoms in the alkyl moiety and exemplified by methoxycarbonyl, n-butoxycarbonyl or octoxycarbonyl group; the aralkoxycarbonyl group is exemplified by benzyloxycarbonyl group; the aryloxycarbonyl group is exemplified by phenoxycarbonyl group; the carbamoyl group may have a substituent on the nitrogen atom such as a lower alkyl group of 1 to 2 carbon atoms, a cycloalkyl group of 5 to 7 carbon atoms or a substituted or unsubstituted phenyl group and exemplified by ethylcarbamoyl, cyclohexanecarbamoyl, phenylcarbamoyl or chlorophenylcarbamoyl group; the thiocarbamoyl group may have a substituent on the nitrogen atom such as a lower alkyl group of 1 to 2 carbon atoms, a cycloalkyl group of 5 to 7 carbon atoms or a substituted or unsubstituted phenyl group and exemplified by ethylthiocarbamoyl, cyclohexylthiocarbamoyl, phenylthiocarbamoyl or chlorophenylthiocarbamoyl group.

In view of anticoccidial activity, preferable are the following pyridinol derivatives:

A compound in which both $R_1$ and $R_2$ in the formula (I) are hydrogen atom; a compound in which $R_2$ is hydrogen atom and $R_1$ is an alkanoyl group of 2 to 8 carbon atoms, an alkenoyl group of 3 to 8 carbon atoms, a cycloalkanoyl group of 6 to 8 carbon atoms, a furoyl group, a tenoyl group or a benzoyl group unsubstituted or substituted with a methyl or methoxy group; a compound in which $R_1$ is hydrogen atom and $R_2$ is an alkanoyl group of 2 to 8 carbon atoms, an alkenoyl group of 3 to 8 carbon atoms, a cycloalkanoyl group of 6 to 8 carbon atoms or a phosphono group; a compound in which both $R_1$ and $R_2$ may be the same or different, are alkanoyl group of 2 to 8 carbon atoms or alkenoyl group of 3 to 8 carbon atoms.

More preferable are the following pyridinol derivatives:

A compound in which both $R_1$ and $R_2$ in the formula (I) are hydrogen atom; a compound in which $R_2$ is a hydrogen atom and $R_1$ is an alkanoyl group of 2 to 8 carbon atoms; a compound in which $R_1$ is a hydrogen atom and $R_2$ is an alkanoyl group of 2 to 8 carbon atoms or a phosphono group.

The acid adduct salts of the above formula (I) also posses anticoccidial activity.

There is no limitation to the acid so far as salts formed are pharmaceutically acceptable and nontoxic to animals.

Suitable salts of this invention are as follows:
acid adduct salts in which an acid is such inorganic acid as hydrochloric acid, sulfuric acid, nitric acid or phosphoric acid; such an organic acid as acetic acid, propionic acid, lactic acid, oxalic acid, succinic acid, maleic acid, tartaric acid, citric acid, benzoic acid, phthalic acid, terephthalic acid, naphthalene disulfonic acid.

Of the pyridinol derivatives of the above formula (I), representative examples thereof are listed below, but they are not intended to be limiting the scope of this invention.

| Compound No. | Chemical Name |
|---|---|
| 1 | 5-hydroxymethyl-2-methyl-3-pyridinol |
| 2 | 3-acetoxy-5-acetoxymethyl-2-methylpyridine |
| 3 | 2-methyl-3-propionyloxy-5-propionyloxymethyl-pyridine |
| 4 | 3-butyryloxy-5-butyryloxymethyl-2-methylpyridine |
| 5 | 3-hexanoyloxy-5-hexanoyloxymethyl-2-methyl-pyridine |
| 6 | 2-methyl-3-octanoyloxy-5-octanoyl-methyl-pyridine |
| 7 | 3-lauroyloxy-5-lauroyloxymethyl-2-methylpyridine |
| 8 | 2-methyl-3-palmitoyloxy-5-palmitoyloxymethyl-pyridine |
| 9 | 2-methyl-3-stearoyloxy-5-stearoyloxymethyl-pyridine |
| 10 | 3-isobutyryloxy-5-isobutyryloxymethyl-2-methyl-pyridine |
| 11 | 3-isovaleroyloxy-5-isovaleroyloxymethyl-2-methyl-pyridine |
| 12 | 3-isohexanoyloxy-5-isohexanoyloxymethyl-2-methyl-pyridine |
| 13 | 3-acetoxy-2-methyl-5-propionyloxymethylpyridine |
| 14 | 3-acetoxy-5-butyryloxymethyl-2-methylpyridine |
| 15 | 3-acetoxy-2-methyl-5-octanoyloxymethylpyridine |
| 16 | 3-acetoxy-2-methyl-5-palmitoyloxymethylpyridine |
| 17 | 3-acetoxy-2-methyl-5-stearoyloxymethylpyridine |
| 18 | 5-acetoxymethyl-2-methyl-3-palmitoyloxypyridine |
| 19 | 5-acetoxymethyl-2-methyl-3-stearoyloxypyridine |
| 20 | 5-methoxymethyl-2-methyl-3-pyridinol |
| 21 | 5-benzyloxymethyl-2-methyl-3-pyridinol |
| 22 | 5-(p-chlorobenzyloxymethyl)-2-methyl-3-pyridinol |
| 23 | 3-benzyloxy-5-hydroxymethyl-2-methylpyridine |
| 24 | 5-hydroxymethyl-3-methoxy-2-methylpyridine |
| 25 | 3-acetoxy-5-hydroxymethyl-2-methylpyridine |
| 26 | 5-hydroxymethyl-2-methyl-3-propionyloxypyridine |
| 27 | 3-butyryloxy-5-hydroxymethyl-2-methylpyridine |
| 28 | 5-hydroxymethyl-2-methyl-3-valeroyloxypyridine |
| 29 | 3-hexanoyloxy-5-hydroxymethyl-2-methylpyridine |
| 30 | 5-hydroxymethyl-2-methyl-3-octonoyloxypyridine |
| 31 | 5-hydroxymethyl-3-lauroyloxy-2-methylpyridine |
| 32 | 5-hydroxymethyl-2-methyl-3-palmitoyloxypyridine |
| 33 | 5-hydroxymethyl-2-methyl-3-stearoyloxypyridine |
| 34 | 5-hydroxymethyl-3-isobutyryloxy-2-methylpyridine |
| 35 | 3-crotonoyloxy-5-hydroxymethyl-2-methylpyridine |
| 36 | 3-cyclohexanecarbonyloxy-5-hydroxymethyl-2-methylpyridine |
| 37 | 5-hydroxymethyl-2-methyl-3-phenoxyacetoxy-pyridine |
| 38 | 5-hydroxymethyl-2-methyl-3-(α-phenoxypropionyloxy)-pyridine |
| 39 | 3-benzoyloxy-5-hydroxymethyl-2-methylpyridine |
| 40 | 5-hydroxymethyl-3-(p-methoxybenzoyloxy)-2-methylpyridine |
| 41 | 5-hydroxymethyl-3-(o-methoxybenzoyloxy)-2-methylpyridine |
| 42 | 5-hydroxymethyl-2-methyl-3-(p-toluoyloxy)-pyridine |
| 43 | 5-hydroxymethyl-2-methyl-3-(m-toluoyloxy)-pyridine |
| 44 | 5-hydroxymethyl-2-methyl-3-(o-toluoyloxy)-pyridine |
| 45 | 3-(3,5-dimethylbenzoyloxy)-5-hydroxymethyl-2-methylpyridine |
| 46 | 3-(3,4-dimethoxybenzoyloxy)-5-hydroxymethyl-2-methylpyridine |
| 47 | 3-(2,3-dimethoxybenzoyloxy)-5-hydroxymethyl-2-methylpyridine |
| 48 | 3-(p-chlorobenzoyloxy)-5-hydroxymethyl-2-methyl-pyridine |
| 49 | 3-(o-chlorobenzoyloxy)-5-hydroxymethyl-2-methyl-pyridine |
| 50 | 5-hydroxymethyl-2-methyl-3-(p-nitrobenzoyloxy)-pyridine |
| 51 | 3-(p-cyanobenzoyloxy)-5-hydroxymethyl-2-methyl-pyridine |
| 52 | 3-(2-furoyloxy)-5-hydroxymethyl-2-methylpyridine |
| 53 | 5-hydroxymethyl-2-methyl-3-(2-thenoyloxy)pyridine |
| 54 | 5-hydroxymethyl-2-methyl-3-nicotinoyloxypyridine |
| 55 | 3-(p-acetylaminobenzoyloxy)-5-hydroxymethyl-2-methylpyridine |
| 56 | 5-hydroxymethyl-2-methyl-3-(α-naphthoyloxy)-pyridine |
| 57 | 5-acetoxymethyl-2-methyl-3-pyridinol |
| 58 | 2-methyl-5-propionyloxymethyl-3-pyridinol |
| 59 | 5-butyryloxymethyl-2-methyl-3-pyridinol |
| 60 | 2-methyl-5-valeroyloxymethyl-3-pyridinol |
| 61 | 5-hexanoyloxymethyl-2-methyl-3-pyridinol |
| 62 | 2-methyl-5-octanoyloxymethyl-3-pyridinol |
| 63 | 5-lauroyloxymethyl-2-methyl-3-pyridinol |
| 64 | 2-methyl-3-palmitoyloxymethyl-3-pyridinol |
| 65 | 2-methyl-5-stearoyloxymethyl-3-pyridinol |
| 66 | 5-isobutyryloxymethyl-2-methyl-3-pyridinol |
| 67 | 5-crotonoyloxymethyl-2-methyl-3-pyridinol |
| 68 | 5-cyclohexanecarbonyloxymethyl-2-methyl-3-pyridinol |
| 69 | 2-methyl-5-phenoxyacetoxymethyl-3-pyridinol |
| 70 | 5-benzoyloxymethyl-2-methyl-3-pyridinol |
| 71 | 5-(p-methoxybenzoyloxymethyl)-2-methyl-3-pyridinol |
| 72 | 2-methyl-5-(p-toluoyloxymethyl)-3-pyridinol |
| 73 | 5-(p-chlorobenzoyloxymethyl)-2-methyl-3-pyridinol |
| 74 | 5-(o-chlorobenzoyloxymethyl)-2-methyl-3-pyridinol |
| 75 | 5-(p-bromobenzoyloxymethyl)-2-methyl-3-pyridinol |
| 76 | 2-methyl-5-(p-nitrobenzoyloxymethyl)-3-pyridinol |
| 77 | 5-(p-cyanobenzoyloxymethyl)-2-methyl-3-pyridinol |
| 78 | 5-(2-furoyloxymethyl)-2-methyl-3-pyridinol |
| 79 | 2-methyl-5-(N-phenylcarbamoyloxymethyl)-3-pyridinol |
| 80 | 5-(N-p-chlorophenylcarbamoyloxymethyl)-2-methyl-3-pyridinol |
| 81 | 5-(N-cyclohexylcarbamoyloxymethyl)-2-methyl-3-pyridinol |
| 82 | 2-methyl-5-(N-phenylthiocarbamoyloxymethyl)-3-pyridinol |
| 83 | 5-(N-p-chlorophenylthiocarbamoyloxymethyl)-2- |

| Compound No. | Chemical Name |
|---|---|
| | methyl-3-pyridinol |
| 84 | 5-(N-cyclohexanethiocarbamoyloxymethyl)-2-methyl-3-pyridinol |
| 85 | 2-methyl-5-nicotinoyloxymethyl-3-pyridinol |
| 86 | 2-methyl-5-phosphonoxymethyl-3-pyridinol |
| 87 | 5-methoxycarbonyloxymethyl-2-methyl-3-pyridinol |
| 88 | 5-butoxycarbonyloxymethyl-2-methyl-3-pyridinol |
| 89 | 5-benzyloxycarbonyloxymethyl-2-methyl-3-pyridinol |
| 90 | 2-methyl-5-phenoxycarbonyloxymethyl-3-pyridinol |
| 91 | 3-acetoxy-5-benzoyloxymethyl-2-methylpyridine |
| 92 | 3-acetoxy-5-(p-chlorobenzoyloxymethyl)-2-methylpyridine |
| 93 | 3-acetoxy-5-(p-methoxybenzoyloxymethyl)-2-methylpyridine |
| 94 | 3-acetoxy-5-(2-furoyloxymethyl)-2-methylpyridine |
| 95 | 3-acetoxy-5-cyclohexanecarbonyloxymethyl-2-methylpyridine |
| 96 | 5-benzoyloxymethyl-2-methyl-3-propionyloxypyridine |
| 97 | 5-cyclohexanecarbonyloxymethyl-2-methyl-3-valeroyloxypyridine |
| 98 | 5-acetoxymethyl-3-cyclohexanecarbonyloxy-2-methylpyridine |
| 99 | 5-acetoxymethyl-3-crotonoyloxy-2-methylpyridine |
| 100 | 3-acetoxy-5-crotonoyloxymethyl-2-methylpyridine |
| 101 | 3-crotonoyloxy-5-crotonoyloxymethyl-2-methylpyridine |
| 102 | 5-crotonoyloxymethyl-3-cyclohexane-carbonyloxy-2-methylpyridine |
| 103 | 3-crotonoyloxy-5-cyclohexanecarbonyloxymethyl-2-methylpyridine |
| 104 | 3-cyclohexanecarbonyloxy-5-cyclohexanecarbonyloxymethyl-2-methylpyridine |
| 105 | 5-acetoxymethyl-3-benzoyloxy-2-methylpyridine |
| 106 | 5-acetoxymethyl-3-(p-methoxybenzoyloxy)-2-methylpyridine |
| 107 | 3-(3,4-dimethoxybenzoyloxy)-2-methyl-5-propionyloxymethylpyridine |
| 108 | 3-(p-methoxybenzoyloxy)-2-methyl-5-valeroyloxymethylpyridine |
| 109 | 5-hexanoyloxymethyl-2-methyl-3-(p-toluoyloxy)-pyridine |
| 110 | 5-acetoxymethyl-3-(p-chlorobenzoyloxy)-2-methylpyridine |
| 111 | 3-methoxycarbonyloxy-5-methoxycarbonyloxymethyl-2-methylpyridine |
| 112 | 3-butoxycarbonyloxy-5-butoxycarbonyloxymethyl-2-methylpyridine |
| 113 | 3-octoxycarbonyloxy-5-octoxycarbonyloxymethyl-2-methylpyridine |
| 114 | 3-benzyloxycarbonyloxy-5-benzyloxycarbonyloxymethyl-2-methylpyridine |
| 115 | 2-methyl-3-phenoxycarbonyloxy-5-phenoxycarbonyloxymethylpyridine |
| 116 | 3-(2-furoyloxy)-5-(2-furoyloxymethyl)-2-methylpyridine |
| 117 | 2-methyl-3-nicotinoyloxy-5-nicotinoyloxymethylpyridine |
| 118 | 3-benzoyloxy-5-(2-furoyloxymethyl)-2-methylpyridine |
| 119 | 3-benzoyloxy-5-benzoyloxymethyl-2-methylpyridine |
| 120 | 3-(p-chlorobenzoyloxy)-5-(p-chlorobenzoyloxymethyl)-2-methylpyridine |
| 121 | 3-(2-tenoyloxy)-5-(2-tenoyloxymethyl)-2-methylpyridine |
| 122 | 3-ethylcarbamoyloxy-5-ethylcarbamoyloxymethyl-2-methylpyridine |
| 123 | 2-methyl-3-phenylcarbamoyloxy-5-phenylcarbamoyloxymethylpyridine |
| 124 | 3-cyclohexanecarbamoyloxy-5-cyclohexanecarbamoyloxymethyl-2-methylpyridine |
| 125 | 3-ethylthiocarbamoyloxy-5-ethylthiocarbamoyloxymethyl-2-methylpyridine |
| 126 | 2-methyl-3-phenylthiocarbamoyloxy-5-phenylthiocarbamoyloxymethylpyridine |
| 127 | 3-acetoxy-5-methoxycarbonyloxymethyl-2-methylpyridine |
| 128 | 3-acetoxy-2-methyl-5-phenylcarbamoyloxymethylpyridine |
| 129 | 3-acetoxy-5-ethylthiocarbamoyloxymethyl-2-methylpyridine |
| 130 | 3-methoxycarbonyloxy-2-methyl-5-valeroyloxymethylpyridine |
| 131 | 3-methoxycarbonyloxy-2-methyl-5-phenylcarbamoyloxymethylpyridine |
| 132 | 5-acetoxymethyl-3-ethylcarbamoyloxy-2-methylpyridine |
| 133 | 5-methoxycarbonyloxymethyl-2-methyl-3-phenylcarbamoyloxypyridine |
| 134 | 5-(o-carboxybenzoyloxymethyl)-2-methyl-3-pyridinol |

The most preferable group of the pyridinol derivatives of the above formula (I) may include the following compounds:

5-hydroxymethyl-2-methyl-3-pyridinol
5-acetoxymethyl-2-methyl-3-pyridinol
2-methyl-5-propionyloxymethyl-3-pyridinol
5-butyryloxymethyl-2-methyl-3-pyridinol
2-methyl-5-valeroyloxymethyl-3-pyridinol
5-hexanoyloxymethyl-2-methyl-3-pyridinol
2-methyl-5-octanoyloxymethyl-3-pyridinol
2-methyl-5-phosphonoxymethyl-3-pyridinol
3-acetoxy-5-hydroxymethyl-2-methylpyridine From the industrial point of view, the most preferable compound is 5-hydroxymethyl-2-methyl-3-pyridinol.

The "Compound No." as given in the foregoing will be hereinafter frequently referred to.

Among the above illustrated compounds, compounds No. 1 and No. 2 are described in The Journal of the American Chemical Society vol. 69, 2574 pp., (1947), but other compounds have not been known yet.

The above new compounds are readily prepared according to the process described hereinafter.

(A) Process for the preparation of 3-mono ester derivatives of 5-hydroxymethyl-2-methyl-3-pyridinol

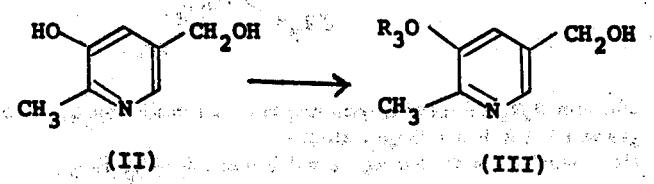

wherein $R_3$ is an aliphatic, an aromatic or a heterocyclic acyl group.

($A_1$) Method with an acid anhydride and water

5-Hydroxymethyl-2-methyl-3-pyridinol (II) or the salt thereof is dissolved in water. In case the salt is used, the solution is neutralized with an equimolar alkali or a tertiary amine.

The reaction is performed by the addition of a saturated or unsaturated aliphatic carboxylic anhydride of 2 to 8 carbon atoms to the solution to form the compounds of formula (III).

($A_2$) Method with an acid halide, an amine and an organic solvent

5-Hydroxymethyl-2-methyl-3-pyridinol (II) or the salt thereof is dissolved or suspended in an aprotic solvent.

The reaction is performed by the addition of an equimolar aliphatic, aromatic or heterocyclic carboxylic halide to the solution in the presence of a tertiary amine under cooling to form the compounds of formula (III).

(A₃) Method with an acid halide and water

To a solution of 5-hydroxymethyl-2-methyl-3-pyridinol (II) or the salt thereof is added an equimolar aklali or a tertiary amine. In case a salt is used, the addition of 2 molar alkali or tertiary amine is necessary for neutralization.

The reaction is performed by the addition of an equimolar aliphatic, aromatic or heterocyclic carboxylic

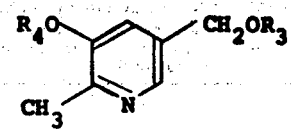

halide to the solution to form the compounds of formula (III).

According to the above process (A), compounds Nos. 25 to 56 are obtained. The examples of the process (A) will be described as referential examples 1 to 4 below.

(B) Process for the preparation of 5-mono-ester derivatives of 5-hydroxymethyl-2-methyl-3-pyridinol

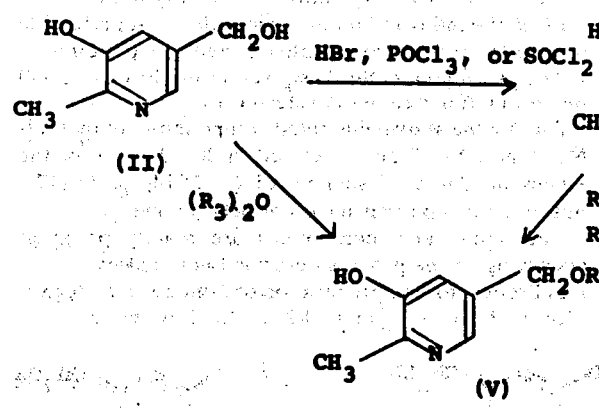

wherein R₃ has the same meaning as described in paragraph (A); X is a halogen atom.

(B₁) Method with 5-halomethyl-2-methyl-3-pyridinol and a silver salt or an organic acid 5-Hydroxymethyl-2-methyl-3-pyridinol (II) or the salt thereof is heated with hydrobromic acid, phosphorus oxychloride or thionyl chloride to form 5-halomethyl-2-methyl-3-pyridinol (IV). The compound (IV) thus obtained is reacted with a silver salt of an organic acid in the corresponding organic acid to form the compound of formula (V).

(B₂) Method with an acid anhydride, an amine and an organic solvent

5-Hydroxymethyl-2-methyl-3-pyridinol or the salt thereof is reacted under heating with an equimolar aliphatic, aromatic or heterocyclic carboxylic anhydride in an aprotic solvent in the presence of pyridine or a tertiary amine to form the compounds of formula (V).

The method is suitable for obtaining 5-mono-ester derivatives in one step in good yield.

(B₃) Method by the selective hydrolysis of 3,5-diesters of 5-hydroxymethyl-2-methyl-3-pyridinol

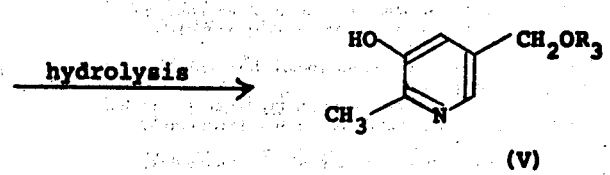

wherein R₃ and R₄, may be the same or different, are aliphatic, aromatic or heterocyclic acyl group.

The 3,5-Diesters of 5-hydroxymethyl-2-methyl-3-pyridinol or the salts thereof are selectively hydrolyzed in the presence of an acid to form the compounds of formula (V).

According to the above process (B), compounds Nos. 57 to 78, No. 85 and No. 134 are obtained. The examples of the process (B) will be described as referential examples 5 to 8 below.

(C) Process for the preparation of 2-methyl-5-phosphonoxymethyl-3-pyridinol

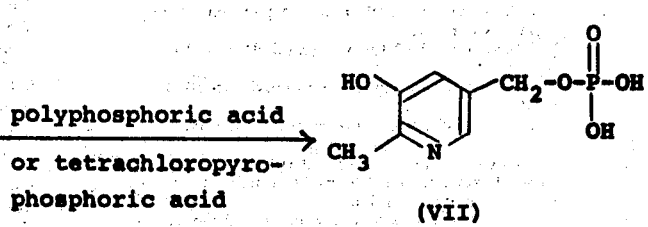

5-Hydroxymethyl-2-methyl-3-pyridinol (II) is reacted with polyphosphoric acid or tetrachloropyrophosphoric acid, the resulting compound is hydrolyzed with an acid to form the compound of formula (VII).

According to the above process (C), compound No. 86 is obtained.

The example of the process (C) will be described as referential example No. 9 and No. 10 below.

(D) Process for the preparation of 5-carbamate and 5-thiocarbamate derivatives of 5-hydroxymethyl-2-methyl-3-pyridinol in an aprotic solvent in the presence of pyridine or a tertiary amine to form the compound of formula (X).

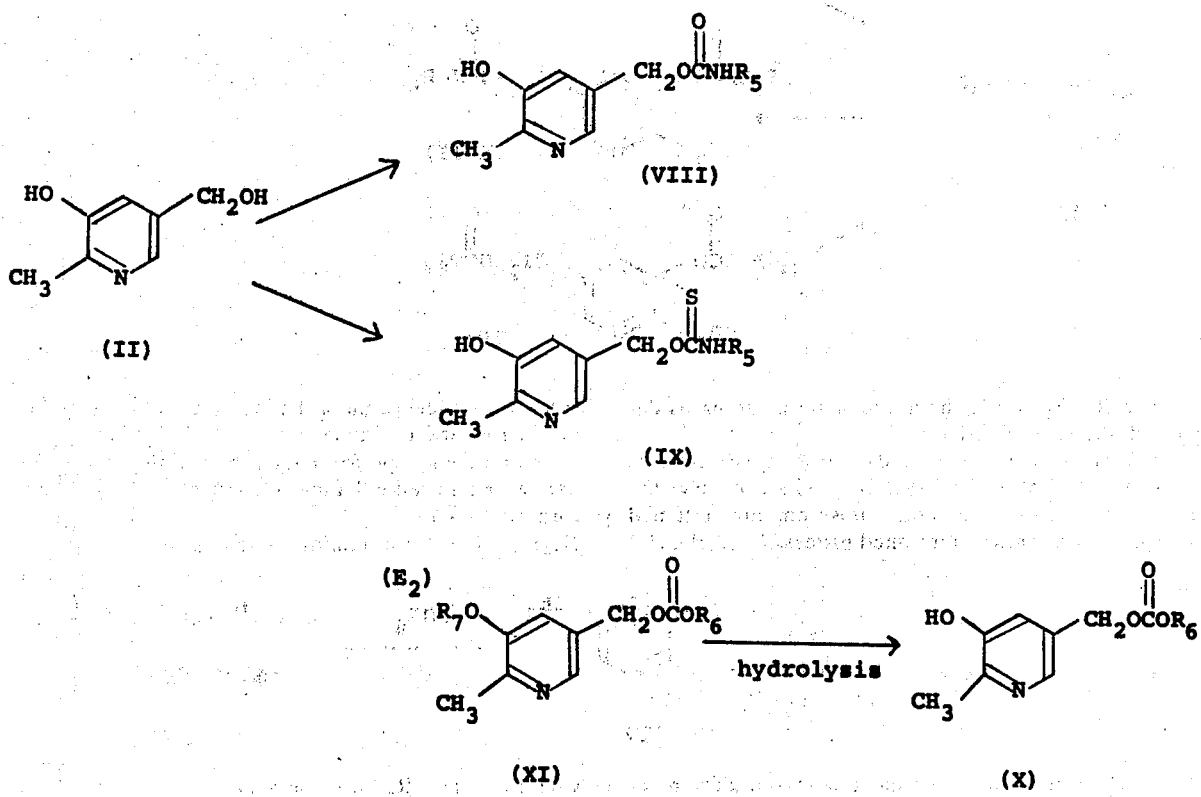

wherein $R_5$ is an alkyl, a cycloalkyl or an aryl group.

5-Hydroxymethyl-2-methyl-3-pyridinol or the salt thereof is dissolved or suspended in an aprotic solvent. The reaction is performed by the addition of an equimolar isocyanate or isothiocyanate to the solution to form the compounds of formula (VIII) or (IX).

According to the above process (D), Compounds Nos. 79 to 85 are obtained.

The example of the process (D) will be described as the referential example 11 below.

(E) Process for the preparation of 5-carbonates of 5-hydroxymethyl-2-methyl-3-pyridinol wherein $R_6$ has the same meaning as described in paragraph $(E_1)$; $R_7$ is an aliphatic acyl group, alkoxycarbonyl group, aralkoxycarbonyl group or an aryloxycarbonyl group.

Compounds of the formula (X) are obtained by the selective hydrolysis of the compounds of the formula (XI) in a diluted acid.

According to the above process (E), compounds No. 87 to 90 are obtained.

The examples of process (E) will be described in referential examples 12 and 13 below.

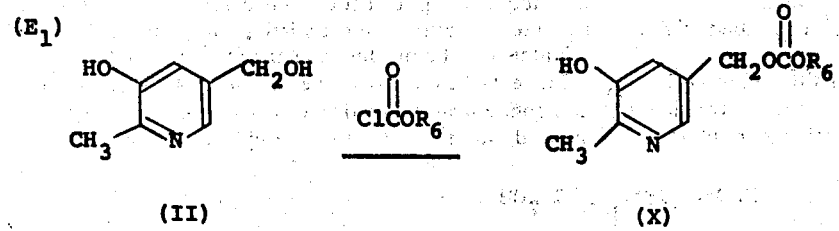

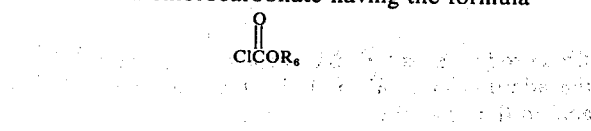

wherein $R_6$ is an alkyl, an aralkyl or an aryl group.

5-Hydroxymethyl-2-methyl-3-pyridinol (II) is reacted with a chlorocarbonate having the formula (F) Process for the preparation of 3,5-disubstituted 5-hydroxymethyl-3-methyl-3-pyridinols (diester, dicarbamate or dicarbonate derivatives having the same substituents on 3- and 5-positions)

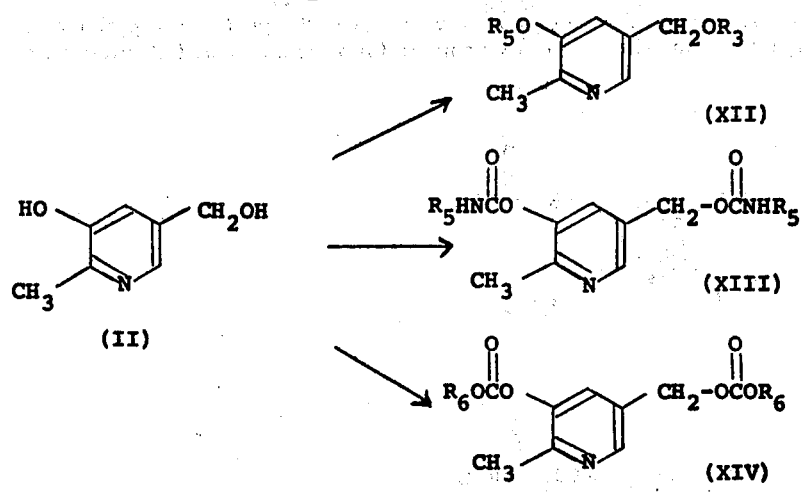

wherein $R_3$, $R_5$ and $R_6$ have the same meaning as described above, respectively.

3,5-Diester, dicarbamate and dicarbonate derivatives of 5-hydroxymethyl-2-methyl-3-pyridinol having the same substituents on 3- and 5-positions are obtained according to the aforementioned process (A), (B), (C) or (D) by using 2 molar or more corresponding reactions.

According to the above process (F), compounds No. 101, No. 104, Nos. 111 to 117 and Nos. 119 to 126 are obtained.

The examples of the process (F) will be described in referential examples 14 to 16 below.

(G) Process for the preparation of 3,5-disubstituted 5-hydroxymethyl-2-methyl-3-pyridinols (diesters, dicarbamates or dicarbonates having the different substituents each other on 3- and 5-positions)

Such compounds are obtained by optional combination of the processes for the preparation of the 3- or 5-substituted derivatives described in (A), (B), (C) or (D).

According to the above process (G), compounds Nos. 91 to 100, No. 102, Nos. 103, Nos. 105 to 110, No. 118 and Nos. 127 to 133 are obtained.

The example of process (G) will be described in the referential example 17.

(H) Process for the preparation of 3- or 5-mono ether derivatives of 5-hydroxymethyl-2-methyl-3-pyridinol (H₁) Method for obtaining 3-mono ether derivatives

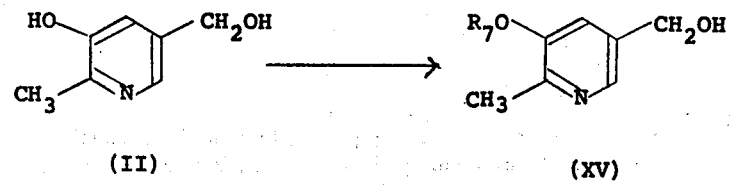

wherein $R_8$ is an alkyl or aralkyl group.

5-Hydroxymethyl-2-methyl-3-pyridinol (II) or the salt thereof is dissolved in dimethylformamide. To the solution is added a metal halide or a metal alcoholate and the solution is stirred.

The reaction is performed by the addition of an alkyl halide or an aralkyl halide to form the compounds of formula (XV).

(H₂) Method for obtaining 5-mono ether derivatives

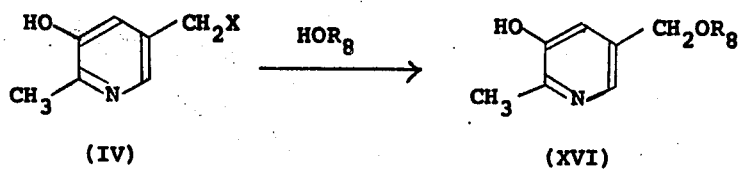

wherein X and $R_8$ have the same meaning as defined above, respectively.

5-Halomethyl-2-methyl-3-pyridinol or the salt thereof is heated with the alcohol of formula $R_8OH$ to form the corresponding compounds of formula (XVI).

According to the above process (H), compounds of Nos. 20 to 24 are obtained.

The examples of process (H) will be described in the referential examples 18 and 19.

REFERENTIAL EXAMPLE 1

3-Acetoxy-5-hydroxymethyl-2-methylpyridine hydrochloride (hydrochloride of No. 25)

To a solution of 3.5 g. 5-hydroxymethyl-2-methyl-3-pyridinol in 15 ml. of water was added 1.7 g. of sodium bicarbonate to neutralize the solution. To the solution was added 2.5 g. of acetic anhydride under stirring at room temperature and the stirring was continued for 20 minutes and the product was taken up in ethyl acetate.

The extract was dried over anhydrous sodium sulfate and concentrated into dryness to give an oil, which was again dissolved in 15 ml. of ethyl acetate and the desired product as colorless crystals was separated out by the addition of 5 ml. of 15% ethanolic hydrochloric acid to the solution.

Yield 3.4 g. m.p. 134°–135°C.

Analysis for $C_9H_{12}ClNO_2$: Calculated: C, 49.61; H, 5.56; N, 6.48. Found: C, 49.82; H, 5.62; N, 6.58.

IR spectrum (Nujol Mull, cm$^{-1}$): $\nu_{OH}$ 3300, $\nu_{C=O}$ 1786.

NMR spectrum ($\tau$, $D_2O$):

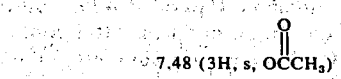
7.48 (3H, s, OCCH$_3$)

7.28 (3H, s, C$_2$—CH$_3$)
5.09 (2H, s, C$_5$—CH$_2$OH)
1.58 (1H, d, J=2.0 C$_4$—H)
1.39 (1H, d, J=2.0 C$_6$—H)

REFERENTIAL EXAMPLE 2

3-Hexanoyloxy-5-hydroxymethyl-2-methylpyridine hydrochloride (hydrochloride of No. 29)

To a solution of 0.9 g. of 5-hydroxymethyl-2-methyl-3-pyridinol hydrochloride in 10 ml. of pyridine was added 0.67 g. of caproyl chloride in 5 ml. of pyridine dropwise under cooling and stirring.

The resulting mixture was stirred overnight at a room temperature, poured into ice water and extracted with ethyl acetate.

The extract was washed with water, dried over anhydrous sodium sulfate and the solvent was distilled off to give an oily residue.

The residue was purified by column chromatography (25 g. of silica gel) and 0.9 g. of an oily substance eluted with benzene-ethyl acetate (7:3 followed by 5:5) was dissolved in ethyl acetate. The desired product as colorless crystals was separated out by the addition of 15% ethanolic hydrochloric acid to the solution.

m.p. 127°–129°C.

Analysis for $C_{13}H_{20}ClNO_3$: Calculated: C, 57.0; H, 7.31; N, 5.12; Cl, 12.97. Found: C, 57.28; H, 7.40; N, 5.33; Cl, 12.99.

IR spectrum (Nujol Mull, cm$^{-1}$): $\nu_{OH}$ 3260, $\nu_{C=O}$ 1770.

NMR spectrum ($\tau$, $D_2O$):

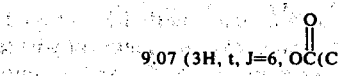
9.07 (3H, t, J=6, OC(CH$_2$)$_4$CH$_3$)

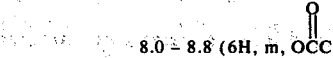
8.0 – 8.8 (6H, m, OCCH$_2$(CH$_2$)$_2$CH$_3$)

7.33 (3H, s, C$_2$—CH$_3$)

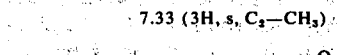
7.17 (2H, t, J=7.5, OCCH$_2$(CH$_2$)$_2$CH$_3$)

5.10 (2H, s, C$_5$—CH$_2$OH)

1.62 (1H, d, J=1.5, C$_4$—H)

1.37 (1H, d, J=1.5, C$_6$—H)

REFERENTIAL EXAMPLE 3

3-Hexanoyloxy-5-hydroxymethyl-2-methylpyridine hydrochloride (hydrochloride of No. 29)

To a solution of 0.9 g. of 5-hydroxymethyl-2-methyl-3-pyridinol hydrochloride and 1.0 g. of triethylamine in 10 ml. of water was added 0.67 g. of n-caproyl chloride dropwise under stirring. After the stirring was continued for 30 minutes, the resulting mixture was extracted with ethyl acetate.

The extract was washed successively with 5% sodium bicarbonate and water and dried over anhydrous sodium sulfate. After the extract was concentrated, the desired product as colorless crystals was separated out by the addition of 15% ethanolic hydrochloric acid. Yield 0.7 g., melting point 127°–129°C.

The IR spectrum of the above compound coincided with that of the standard.

REFERENTIAL EXAMPLE 4

5-Hydroxymethyl-3-(p-methoxybenzoyloxy)-2-methylpyridine (No. 40)

To a solution of 0.9 g. of 5-hydroxymethyl-2-methyl-3-pyridinol hydrochloride in 5 ml. of anhydrous pyridine was added 0.86 g. of p-anisoyl chloride dropwise under cooling. After standing overnight the resulting mixture was poured into ice water and extracted with chloroform.

The extract was washed with water and dried over anhydrous sodium sulfate. 1.4 g. of the desired product as colorless crystals was obtained by removing the solvent and recrystallization from ethyl acetate and n-hexane.

m.p. 103°–104°C.

Analysis for $C_{15}H_{15}NO_4$: Calculated: C, 65.92; H, 5.53; N, 5.13. Found: C, 65.82; H, 5.50; N, 5.01.

IR spectrum (Nujol Mull, cm$^{-1}$) $\nu_{OH}$ 3200, $\nu_{C=O}$ 1730.

NMR spectrum ($\tau$, CDCl$_3$):

7.56 (3H, s, C$_2$—CH$_3$)
6.34 (1H, broad W1/2=10, OH)
6.11 (3H, s, OCH$_3$)
5.30 (2H, s, C$_5$—CH$_2$OH)

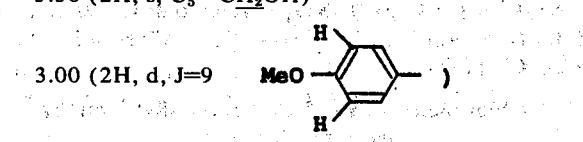
3.00 (2H, d, J=9

2.43 (1H, d, J=1.5, C$_4$—H)

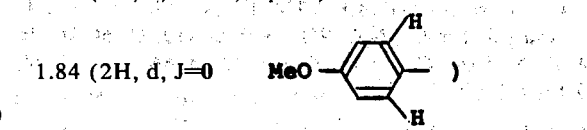
1.84 (2H, d, J=0

1.70 (1H, d, J=1.5, C$_6$—H)

Following the substantially same procedure as shown in the referential examples 1 to 4, those pyridine derivatives as recited below were prepared:

5-Hydroxymethyl-2-methyl-3-octanoyloxypyridine (No. 30)

Colorless oil,

R$_f$ value of thin-layer chromatography: 0.63
(Plate, Dc-Fertig Platten Kieselgel available from Merck Co. Ltd., Developing solvent, ethyl acetate)

Analysis for $C_{15}H_{23}NO_3$: Calculated: C, 67.89; H, 8.74; N, 5.28. Found: C, 67.47; H, 8.49; N, 5.16.

IR spectrum (liquid, cm$^{-1}$): $\nu_{OH}$ 3200, $\nu_{C=O}$ 1760.

5-Hydroxymethyl-2-methyl-3-palmitoyloxypyridine (No. 32)

Colorless crystal, m.p. 58°–60°C.
Analysis for $C_{23}H_{39}NO_3$: Calculated: C, 73.16; H, 10.41; N, 3.71. Found: C, 73.59; H, 10.88; N, 3.51.

3-Cyclohexanecarbonyloxy-5-hydroxymethyl-2-methylpyridine hydrochloride (hydrochloride of No. 36)

Colorless crystal, m.p. 148°–150°C.
Analysis for $C_{14}H_{20}ClNO_3$: Calculated: C, 58.8; H, 7.0; N, 4.9; Cl, 12.43. Found: C, 59.1; H, 7.1; N, 4.96; Cl, 12.64.

5-Hydroxymethyl-2-methyl-3-methyl-3-(-phenoxypropionyloxy)pyridine hydrochloride (hydrochloride of No. 38)

Colorless crystal, m.p. 134°–136°C.
Analysis for $C_{16}H_{18}ClNO_4$: Calculated: C, 59.3; H, 5.57; N, 4.32; Cl, 10.96. Found: C, 59.0; H, 5.53; N, 4.14; Cl, 11.15.

3-Benzoyloxy-5-hydroxymethyl-2-methylpyridine (No. 39)

Colorless crystal, m.p. 81°–83°C.
Analysis for $C_{14}H_{13}NO_3$: Calculated: C, 69.12; H, 5.39; N, 5.76. Found: C, 69.08; H, 5.36; N, 5.60.

5-Hydroxymethyl-2-methyl-3-(p-toluoyloxy)pyridine (No. 42)

Colorless crystal, m.p. 80°–81°C.
Analysis for $C_{15}H_{15}NO_3$: Calculated: C, 70.02; H, 5.88; N, 5.44. Found: C, 69.88; H, 5.74; N, 5.26.

3-(p-Chlorobenzoyloxy)-5-hydroxymethyl-2-methylpyridine (No. 48)

Colorless crystal, m.p. 108°–109°C.
Analysis for $C_{14}H_{12}ClNO_3$: Calculated: C, 60.5; H, 5.32; N, 5.04; Cl, 12.78. Found: C, 60.47; H, 4.32; N, 5.22; Cl, 12.97.

3(o-Chlorobenzoyloxy)-5-hydroxymethyl-2-methylpyridine (No. 49)

Colorless crystal, m.p. 72°–74°C.
Analysis for $C_{14}H_{12}ClNO_3$: Calculated: C, 60.50; H, 4.32; N, 5.04; Cl, 12.78. Found: C, 60.66; H, 4.32; N, 5.11; Cl, 12.71.

5-Hydroxymethyl-2-methyl-3-(p-nitrobenzoyloxy)pyridine (No. 50)

Colorless crystal, m.p. 165°–167°C.
Analysis for $C_{14}H_{12}N_2O_5$: Calculated: C, 58.33; H, 4.20; N, 9.72. Found: C, 58.16; H, 4.14; N, 9.55.

3-(2-Furoyloxy)-5-hydroxymethyl-2-methylpyridine (No. 52)

Colorless oil
Analysis for $C_{12}H_{11}NO_4$: Calculated: C, 61.80; H, 4.75; N, 6.01. Found: C, 61.63; H, 4.93; N, 5.97.
IR spectrum (liquid, cm$^{-1}$): $\nu_{OH}$ 3205, $\nu_{C=O}$ 1742.

5-Hydroxymethyl-2-methyl-3-(α-naphthoyloxy)-pyridine (No. 56)

Colorless oil,
$R_f$ value of thin-layer chromatography 0.46 (Developing solvent, ethyl acetate)

Analysis for $C_{18}H_{15}NO_3$: Calculated: C, 73.70; H, 5.15; N, 4.78. Found: C, 73.50; H, 5.04; N, 4.97.

REFERENTIAL EXAMPLE 5

5-Acetoxymethyl-2-methyl-3-pyridinol (No. 57)

2.0 g. of 5-hydroxymethyl-2-methyl-3-pyridinol hydrochloride was suspended in 10 ml. of 47% hydrobromic acid and refluxed for 30 minutes. After cooling the solution was made alkaline with aqueous sodium bicarbonate solution to give 1.2 g. of the crystalline product.

The crystal was added to a solution of 3.5 g. of silver acetate and 22 g. of potassium acetate in 80 ml. of acetic acid and kept at 130°–150°C. for 1.5 hours.

The acetic acid in the solution was distilled off and the resulting residue was diluted with water and extracted with ethyl acetate.

The extract was washed with water and dried.

The desired product was obtained by removing the solvent followed by the recrystallization from ethyl acetate.

Colorless crystal, m.p. 170°–172°C.
Analysis for $C_9H_{11}NO_3$: Calculated: C, 59.66; H, 6.12; N, 7.73. Found: C, 59.83; H, 6.03; N, 7.78.
IR spectrum (Nujol Mull, cm$^{-1}$): $\nu_{OH}$ 2634, 2500 $\nu_{C=O}$ 1757.

NMR spectrum ($\tau$, $(CD_3)_2NC\diagdown_O^D$)

7.92 (3H, s, O—$\overset{O}{\underset{\|}{C}}$CH$_3$)

7.60 (3H, s, C$_2$—CH$_3$)

4.92 (2H, s, C$_5$—C$\underline{H}_2$OAc)

2.29 (1H, d, J=2.0, C$_4$—H)

2.20 (1H, d, J=2.0, C$_6$—H)

REFERENTIAL EXAMPLE 6

2-Methyl-5-valeroyloxymethyl-3-pyridinol (No. 60)

A solution of 0.9 g. of 5-hydroxymethyl-2-methyl-3-pyridinol hydrochloride and 0.95 g. of valeic anhydride in 5 ml. of pyridine was kept at 120°C for 20 hours under stirring.

The solution was poured into ice water and extracted with ethyl acetate and the extract was washed with water, dried over anhydrous sodium sulfate and the solvent was distilled off to give a crystalline substance.

The substance was recrystallized from ethyl acetate and n-hexane to give 1.1 g. of the desired product.

Colorless crystal, m.p. 114°–115°C.
Analysis for $C_{12}H_{17}NO_3$: Calculated: C, 64.55; H, 7.68; N, 6.27. Found: C, 64.64; H, 7.68; N, 6.55.
IR spectrum (Nujol Mull, cm$^{-1}$): $\nu_{OH}$ 2600, 2500, $\nu_{C=O}$ 1730.
NMR spectrum ($\tau$, CDCl$_3$):

9.12 (3H, t, J=6, O$\overset{O}{\underset{\|}{C}}$(CH$_2$)$_3$C$\underline{H}_3$)

8.2 – 8.9 (4H, m, O$\overset{O}{\underset{\|}{C}}$CH$_2$C$\underline{H}_2$C$\underline{H}_2$CH$_3$)

7.65 (2H, t, OCC$\underline{H}_2$CH$_2$CH$_2$CH$_3$)

7.41 (3H, s, C$_2$—C$\underline{H}_3$)

4.91 (2H, s, C$_5$—C$\underline{H}_2$OCR)

2.74 (1H, d, J=1.5, C$_4$—H)

1.97 (1H, d, J=1.5, C$_6$—H)

—2.8 (1H, broad, OH)

REFERENTIAL EXAMPLE 7

5-Benzoyloxymethyl-2-methyl-3-pyridinol (No. 70)

0.5 g. of 3-acetoxy-5-benzoyloxymethyl-2-methyl pyridine was added to 25 ml. of 2N hydrochloric acid and stirred for 1 hour at 80°C, during which time the mixture was one dissolved, then a crystal was separated out.

The reaction mixture was neutralized with potassium bicarbonate and filtered off.

The crystal separated was recrystallized from ethanol to give 0.2 g. of the desired product as colorless-crystals.

m.p. 221°–223°C.

Analysis for C$_{14}$H$_{13}$NO$_3$: Calculated: C, 69.12; H, 5.39; N, 5.76. Found: C, 69.18; H, 5.30; N, 5.66.

IR spectrum (Nujol Mull, cm$^{-1}$): $\nu_{OH}$ 2500, $\nu_{C=O}$ 1720.

NMR spectrum ($\tau$, CF$_3$COOH):

7.18 (3H, s, C$_2$—CH$_3$)

4.35 (2H, s, 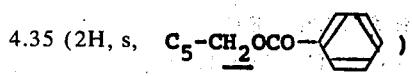 )

2.15–2.50 (3H, m, Aromatic H)
1.90 (1H, d, J=2.0, C$_4$—$\underline{H}$)
1.76 (1H, d, J=2.0, C$_6$—$\underline{H}$)
1.60–1.95 (2H, m, Aromatic H)

REFERENTIAL EXAMPLE 8

5-(2-Furoyloxymethyl)-2-methyl-3-pyridinol (No. 78)

0.98 G. of 3-(2-furoyloxy)-5-(2-furoyloxymethyl)-2-methylpyridine was heated at 75°C for 1 hour in 20 ml. of 2N hydrochloric acid.

The solvent was distilled off under reduced pressure, and the residue was diluted with 20 ml. of water and neutralized with sodium bicarbonate and extracted with ethyl acetate.

The extract was washed successively with an aqueous solution of sodium bicarbonate and water and after dried over anhydrous sodium sulfate the solvent was distilled off.

The resulting residue was purified by silica gel chromatography and 0.46 g. of the desired product as colorless crystals was obtained from the eluate with ethyl acetate.

m.p. 192°C.

Analysis for C$_{12}$H$_{11}$NO$_4$: Calculated: C, 61.80; H, 4.75; N, 6.01. Found: C, 61.65; H, 4.58; N, 5.96.

IR spectrum (Nujol Mull, cm$^{-1}$): $\nu_{OH}$ 2500, $\nu_{C=O}$ 1730.

NMR spectrum ($\tau$ (CD$_3$)$_2$SO):

7.64 (3H, s, C$_2$—CH$_3$)
4.70 (2H, s, C$_5$—CH$_2$OCOR)
3.27 (1H, q, J=3.5, 1.0 Furan C$_4$—H)
2.75 (1H, d, J=2.0, C$_4$—H)
2.62 (1H, q, J=3.5, 1.0, Furan C$_3$—H)
1.85–2.02 (2H, broad, C$_6$—H of the pyridinol and C$_5$—H of the furan ring are overlapped)

Following the substantially same procedure as shown in referential examples 5–8, those pyridine derivatives as recited below were prepared.

2-Methyl-5-propionyloxymethyl-3-pyridinol (No. 58)

Colorless crystal, m.p. 149°–150°C.

Analysis for C$_{10}$H$_{13}$NO$_3$: Calculated: C, 61.52; H, 6.71; N, 7.18. Found: C, 61.59; H, 6.76; N, 7.36.

2-Methyl-5-octanoyloxymethyl-3-pyridinol (No. 62)

Colorless crystal, m.p. 107°–108°C.

Analysis for C$_{15}$H$_{23}$NO$_3$:
Calculated: C, 67.89; H, 8.74; N, 5.28. Found: C, 67.87; H, 8.64; N, 5.06.

5-Isobutyryloxymethyl-2-methyl-3-pyridinol (No. 66)

Colorless crystal, m.p. 143°–145°C.

Analysis for C$_{11}$H$_{15}$NO$_3$: Calculated: C, 63.14; H, 7.23; N, 6.69. Found: C, 63.49; H, 7.00; N, 6.77.

5-Crotonoyloxymethyl-2-methyl-3-pyridinol (No. 67)

Colorless crystal, m.p. 150°–153°C.

Analysis for C$_{11}$H$_{13}$NO$_3$: Calculated: C, 63.75; H, 6.33; N, 6.77. Found: C, 63.62; H, 6.35; N, 6.93.

5-(p-Methoxybenzoyloxymethyl)-2-methyl-3-pyridinol hydrochloride (hydrochloride of No. 71)

Colorless crystal, m.p. 221°–223°C (dec).

Analysis for C$_{15}$H$_{13}$ClNO$_4$: Calculated: C, 58.70; H, 4.24; N, 4.56; Cl, 11.56. Found: C, 58.59; H, 4.60; N, 4.5; Cl, 11.90.

5-Cyclohexanecarbonyloxymethyl-2-methyl-3-pyridinol (No. 68)

Colorless crystal, m.p. 173°–175°C.

Analysis for C$_{14}$H$_{19}$NO$_3$: Calculated: C, 67.44; H, 7.68; N, 5.62. Found: C, 67.20; H, 7.66; N, 5.76.

2-Methyl-5-(p-nitrobenzoyloxymethyl)-3-pyridinol hydrochloride (hydrochloride of No. 76)

Colorless crystal, m.p. 210°C.

Analysis for C$_{14}$H$_{13}$ClN$_2$O$_5$: Calculated: C, 51.70; H, 4.02; N, 8.63; Cl, 10.94. Found: C, 51.52; H, 3.78; N, 8.75; Cl, 10.96.

REFERENTIAL EXAMPLE 9

2-Methyl-5-phosphonoxymethyl-3-pyridinol (No. 86)

2.6 G. of 5-hydroxymethyl-2-methyl-3-pyridinol was added to 15 g. of polyphosphoric acid and the mixture was heated at 90°C for 5 hours. After the completion of the reaction, the resulting mixture was diluted with 30 ml. of water and heated for one hour at 100°C to hydrolyze the resulting polyester to the monoester.

After cooling, the mixture was neutralized with barium carbonate and the precipitate formed was filtered off.

The filtrate was concentrated under reduced pressure and adjusted to pH 2.5–3.0.

The crystal separated out by cooling was filtered and recrystallized from water-acetone and dried at 70°–80°C to give 0.42 g. of the desired product as colorless crystals.

Analysis for $C_7H_{10}NO_5P$: Calculated: C, 38.41; H, 4.60; N, 6.40; P, 14.02. Found: C, 38.44; H, 4.55; N, 6.16; P, 13.82.

IR spectrum (Nujol Mull, cm$^{-1}$): $\nu_{OH}$ 2500, $\nu_{C-O-P}$ 1030.

NMR spectrum ($\tau$, $D_2O$, DCl):
7.32 (3H, s, $C_2$—$CH_3$)
4.85 (2H, s, $C_5$—$CH_2OPO_3H_2$)
2.02 (1H, d, J=2.0 $C_4$—H)
1.72 (1H, d, J=2.0 $C_6$—H)

REFERENTIAL EXAMPLE 10

2-Methyl-5-phosphonoxymethyl-3-pyridinol (No. 86)

1.3 G. of 5-hydroxymethyl-2-methyl-3-pyridinol was added to 5.0 g. of tetrachloropyrophosphoric acid cooled to −10°C under stirring. After the additional stirring for 2 hours, the mixture was allowed to stand overnight at 0°C, then diluted with 100 ml. of 1N hydrochloric acid. Thereafter, following the substantially same procedure as shown in referential example 9, 0.2 g. of the desired product was obtained.

REFERENTIAL EXAMPLE 11

2-Methyl-5-(N-phenylcarbamoyloxymethyl)-3-pyridinol (No. 79)

To a solution of 0.9 g. of 5-hydroxymethyl-2-methyl-3-pyridinol hydrochloride in 5 ml. of pyridine was added 0.3 g. of phenylisocyanate and the mixture was stirred at room temperature for 15 hours. After the pyridine was distilled off under reduced pressure, the resulting residue was poured into 15 ml. of water, neutralized with sodium bicarbonate and extracted with ethyl acetate.

The extract was dried over anhydrous sodium sulfate and the solvent was distilled off. The resulting crystal was recrystallized from ethyl acetate and ether to give 0.55 g. of the desired product.

as colorless crystals, m.p. 195°–196°C.

Analysis for $C_{14}H_{14}NO_3$: Calculated: C, 65.10; H, 5.46; N, 10.85. Found: C, 64.98; H, 5.39; N, 10.76.

IR spectrum (Nujol Mull, cm$^{-1}$): $\nu_{NH}$ 3356, $\nu_{OH}$ 2650, $\nu_{C=O}$ 1715.

NMR spectrum ($\tau$, $(CD_3)_2SO$):
7.67 (3H, s, $C_2$—$CH_3$)
4.89 (2H, s, $C_5$—$CH_2O$)
2.23–3.03 (6H, m, $\overline{NH}$ and aromatic H)
2.0 (1H, d, J=2.0, $C_4$—H)
1.17 (1H, d, J=2.0, $C_6$—H)

REFERENTIAL EXAMPLE 12

5-Methoxycarbonyloxymethyl-2-methyl-3-pyridinol (No. 87)

To a solution of 1.8 g. of 5-hydroxymethyl-2-methyl-3-pyridinol hydrochloride in 10 ml. of pyridine was added 1.0 g. of methyl chlorocarbonate dropwise under cooling. After standing overnight, the reaction mixture was poured into ice water and extracted with ethyl acetate. The extract was washed with water, dried and the solvent was distilled off to give 1.0 g. of an oily substance. The oily substance was purified by column chromatography (silica gel 20 g.) and 0.6 g. of the desired product as colorless crystal was obtained from the eluate with benzene-ethyl acetate (3:7) and recrystallized from ethyl acetate and n-hexane.

Colorless crystal, m.p. 187°–188°C (dec).

Analysis for $C_9H_{11}NO_4$: Calculated: C, 54.82; H, 5.62; N, 7.10. Found: C, 55.02; H, 5.91; N, 7.47.

IR spectrum (Nujol Mull, cm$^{-1}$): $\nu_{OH}$ 2500, $\nu_{C=O}$ 1740.

NMR spectrum ($\tau$, $(CD_3)_2NC\underset{D}{\overset{O}{\diagup}}$)

7.60 (3H, s, $C_2$—$CH_3$)
6.22 (3H, s, $COOCH_3$)
4.84 (2H, s, $C_5$—$CH_2OCOOCH_3$)
2.72 (1H, d, J=2, $C_4$—H)
1.95 (1H, d, J=2, $C_6$—H)

REFERENTIAL EXAMPLE 13

5-Methoxycarbonyloxymethyl-2-methyl-3-pyridinol (No. 87)

A solution of 1 g. of 3-methoxycarbonyloxy-5-methoxycarbonyloxymethyl-2-methylpyridine in an aqueous ethanol (10 ml. of ethanol and 5 ml. of water) was adjusted to pH 1–1.5 with 10% hydrobromic acid. The mixture was heated at 90°C for 30 minutes, then cooled and neutralized with sodium bicarbonate and extracted with ethyl acetate. The extract was dried over anhydrous sodium sulfate and concentrated into a small volume and the addition of n-hexane gave 0.45 g. of the desired product as colorless crystals melting at 187°–189°C, which showed no depression of melting point on admixture with the authentic sample and the IR spectrum coincided with that of the standard completely.

REFERENTIAL EXAMPLE 14

2-(2-Furoyloxy)-5-(2-furoyloxymethyl)-2-methylpyridine (No. 116)

To a solution of 0.9 g. of 5-hydroxymethyl-2-methyl-3-pyridinol hydrochloride in 15 ml. of pyridine was added 1.3 g. of furoyl chloride and the mixture was stirred at room temperature for 15 hours. Pyridine was distilled off under reduced pressure and the residue was poured into 15 ml. of water, neutralized with sodium bicarbonate and extracted with ethyl acetate. The extract was dried over anhydrous sodium sulfate an oily substance obtained by removal of the solvent was crystallized from ethanol to give 1.5 g. of the desired product.

Colorless crystal, m.p. 118°–119°C.

Analysis for $C_{17}H_{13}NO_6$: Calculated: C, 62.38; H, 4.00; N, 4.28. Found: C, 62.75; H, 4.21; N, 4.14.

IR spectrum (Nujol Mull, cm$^{-1}$): $\nu_{C=O}$ 1740.

Following the substantially same procedure as described in the above referential example 14, those pyridine derivatives as recited below were prepared:

3-Acetoxy-5-acetoxymethyl-2-methylpyridine hydrochloride (hydrochloride of No. 2)

Colorless crystal, m.p. 122°–125°C.

Analysis for $C_{11}H_{14}ClNO_4$: Calculated: C, 50.80; H, 5.39; N, 5.39; Cl, 13.66. Found: C, 56.68; H, 5.52; N, 5.40; Cl, 13.43.

IR spectrum (Nujol Mull, cm$^{-1}$): $\nu_{C=O}$ 1770, 1740.

2-Methyl-3-propionyloxy-5-propionyloxymethylpyridine (No. 3)

Colorless oil

Analysis for C₁₃H₁₇NO₄: Calculated: C, 62.14; H, 6.82; N, 5.57. Found: C, 62.10; H, 6.80; N, 5.62.
IR spectrum (liquid film, cm⁻¹): $\nu_{C=O}$ 1770, 1750.

3-Butyryloxy-5-butyryloxymethyl-2-methylpyridine (No. 4)

Colorless oil,
Analysis for C₁₅H₂₁NO₄: Calculated: C, 64.49; H, 7.58; N, 5.01. Found: C, 64.20; H, 7.59; N, 5.11.
IR spectrum (liquid film, cm⁻¹): $\nu_{C=O}$ 1764, 1742.

3-Isobutyryloxy-5-isobutyryloxymethyl-2-methylpyridine hydrochloride (hydrochloride of No. 10)

Colorless crystal, m.p. 134°–136°C.
Analysis for C₁₅H₂₂ClNO₄: Calculated: C, 57.10; H, 6.97; N, 4.43; Cl, 11.25. Found: C, 57.14; H, 6.94; N, 4.77; Cl, 11.27.
IR spectrum (Nujol Mull, cm⁻¹): $\nu_{C=O}$ 1738, 1762.

3-Cyclohexanecarbonyloxy-5-cyclohexanecarbonyloxymethyl-2-methylpyridine hydrochloride (hydrochloride of No. 104)

Colorless crystal, m.p. 148°–151°C.
Analysis for C₂₁H₃₀ClNO₄: Calculated: C, 63.7; H, 7.58; N, 3.54; Cl, 8.97. Found: C, 64.0; H, 7.67; N, 3.85; Cl, 8.95.

3-Crotonoyloxy-5-crotonoyloxymethyl-2-methylpyridine (No. 101)

Colorless oil,
Analysis for C₁₅H₁₇NO₄: Calculated: C, 65.44; H, 6.22; N, 5.09. Found: C, 65.40; H, 6.16; N, 5.32.
IR spectrum (liquid film, cm⁻¹): $\nu_{C=O}$ 1740, 1720.

3-Benzoyloxy-5-benzoyloxymethyl-2-methylpyridine (No. 119)

Colorless crystal, m.p. 85°–86°C.
Analysis for C₂₁H₁₇NO₄: Calculated: C, 72.61; H, 4.93; N, 4.03. Found: C, 72.63; H, 4.83; N, 4.33.

3-(p-Chlorobenzoyloxy)-5-(p-chlorobenzoyloxymethyl)-2-methylpyridine (No. 120)

Colorless crystal, m.p. 157°–159°C.
Analysis for C₂₁H₁₅Cl₂NO₄: Calculated: C, 60.40; H, 3.61; N, 3.37; Cl, 17.09. Found: C, 60.23; H, 3.78; N, 3.36; Cl, 16.84.

REFERENTIAL EXAMPLE 15

3-Ethylcarbamoyloxy-5-ethylcarbamoyloxymethyl-2-methylpyridine (No. 122)

To a solution of 0.9 g. of 5-hydroxymethyl-2-methyl-3-pyridinol hydrochloride in 10 ml. of pyridine was added 0.8 g. of ethyl isocyanate and the mixture was stirred at 100°C for 2 hours. After cooling, the mixture was poured into ice water and extracted with chloroform. The extract was washed with water, dried over anhydrous sodium sulfate and the solvent was distilled off to give a crystalline product, which was recrystallized from ethyl acetate-n-hexane to give 0.95 g. of the desired product as colorless crystals.
m.p. 121°–122°C.
Analysis for C₁₃H₁₉N₃O₄: Calculated: C, 55.50; H, 6.81; N, 14.94. Found: C, 55.10; H, 6.74; N, 15.20.
IR spectrum (Nujol Mull, cm⁻¹): $\nu_{NH}$ 3330, $\nu_{C=O}$ 1710, 1690.
NMR spectrum (τ, CDCl₃):
8.88 (3H, t, J=7)
8.77 (3H, t, J=7)
7.55 (3H, s, C₂—CH₃)
6.5–7.0 (4H, m)
4.90 (2H, s, C₅—CH₂)
4.90 (1H, broad, NH)
4.50 (1H, broad, NH)
2.52 (1H, d, J=2.0, C₄—H)
1.67 (1H, d, J=2.0, C₆—H)

REFERENTIAL EXAMPLE 16

3-Methoxycarbonyloxy-5-methoxycarbonyloxymethyl-2-methylpyridine (No. 111)

To a solution of 0.9 g. of 5-hydroxymethyl-2-methyl-3-pyridinol hydrochloride in 10 ml. of pyridine was added 1.0 g. of methyl chlorocarbonate dropwise under cooling. After standing overnight, the reaction mixture was poured into ice water and extracted with ethyl acetate.
The extract was washed with water, dried over anhydrous sodium sulfate and the solvent was distilled off. The resulting residue was recrystallized from ethyl acetate and n-hexane to give 0.6 g. of the desired product as colorless crystals.
m.p. 65°C.
Analysis for C₁₁H₁₃NO₆: Calculated: C, 51.76; H, 5.49; N, 5.49. Found: C, 52.08; H, 5.31; N, 5.69.
IR spectrum (Nujol Mull, cm⁻¹): $\nu_{C=O}$ 1750.
NMR spectrum (τ, CDCl₃):
7.52 (3H, s, C₂—CH₃)
6.20 (3H, s, COOCH₃)
6.06 (3H, s, COOCH₃)
4.82 (2H, s, C₅—CH₂OCOOCH₃)
2.42 (1H, d, J=2.0, C₄—H)
1.57 (1H, d, J=2.0, C₆—H)

REFERENTIAL EXAMPLE 17

3-Acetoxy-5-benzoyloxymethyl-2-methylpyridine (No. 91)

To a solution of 1.1 g. of 3-acetoxy-5-hydroxymethyl-2-methylpyridine hydrochloride in 10 ml. of pyridine was added 0.8 g. of benzoyl chloride dropwise under cooling.
The mixture was stirred overnight at room temperature, then poured into ice water and extracted with ethyl acetate. The extract was washed with water, dried and the solvent was distilled off to give an oily substance, which was purified by column chromatography (silica gel 30 g.) An oily substance obtained from the eluate with benzene-ethyl acetate (8:2) was crystallized from ethyl acetate and n-hexane to give 1.35 g. of the desired product as colorless crystals.
m.p. 57°C
Analysis for C₁₆H₁₅NO₄: Calculated: C, 67.36; H, 5.30; N, 4.91. Found: C, 67.36; H, 5.17; N, 4.82.
IR spectrum (Nujol Mull, cm⁻¹): $\nu_{C=O}$ 1760, 1720.
NMR spectrum (τ, CDCl₃):

7.65 (3H, s, OCCH₃ [O])
7.55 (3H, s, C₂—CH₃)
4.62 (2H, s, 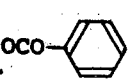 )

2.3–2.6 (4H, m, Aromatic H)
1.85–2.0 (1H, m, Aromatic H)
1.83 (1H, d, J=2.0, C$_4$—H)
1.52 (1H, d, J=2.0, C$_6$—H)

Following the substantially same procedure as shown in referential example 17, those pyridinol derivatives recited below were prepared.

3-Acetoxy-5-(p-methoxybenzoyloxymethyl)-2-methylpyridine (No. 93)

Colorless crystal, m.p. 65°–66°C.

Analysis for C$_{17}$H$_{17}$NO$_5$: Calculated: C, 64.75; H, 5.43; N, 4.44. Found: C, 64.71; H, 5.40; N, 4.12.

3-Acetoxy-5-(2-furoyloxymethyl)-2-methylpyridine (No. 94)

Colorless oil

R$_f$ value of thin-layer chromatography: 0.76
(Plate, Dc-Fertig platten Kieselgel available from Merck Co., Ltd., Developing solvent, ethyl acetate)

Analysis for C$_{14}$H$_{13}$NO$_5$: Calculated: C, 61.09; H, 4.76; N, 5.09. Found: C, 60.79; H, 4.52; N, 15.35.

5-Acetoxymethyl-3-benzoyloxy-2-methylpyridine hydrochloride (hydrochloride of No. 105)

Colorless crystal, m.p. 148°–150°C.

Analysis for C$_{16}$H$_{16}$ClNO$_4$: Calculated: C, 59.75; H, 4.98; N, 4.36; Cl, 11.02. Found: C, 59.76; H, 5.02; N, 4.63; Cl, 10.81.

3-Acetoxy-5-cyclohexanecarbonyloxymethyl-2-methylpyridine (No. 95)

Colorless oil

Analysis for C$_{16}$H$_{21}$NO$_4$: Calculated: C, 65.95; H, 7.27; N, 4.81. Found: C, 65.83; H, 7.30; N, 4.76.

IR spectrum (liquid film, cm$^{-1}$): $\nu_{C=O}$ 1776, 1736.

REFERENTIAL EXAMPLE 18

3-Benzyloxy-5-hydroxymethyl-2-methylpyridine (No. 23)

To a solution of 1.7 g. of 5-hydroxymethyl-2-methyl-3-pyridinol hydrochloride in 10 ml. of dimethylformamide was added a solution of 0.9 g. of 50% sodium hydride in 6 ml. of dimethylformamide. The mixture was stirred at room temperature for 3 hours and to the solution was added 1.25 g. of benzyl chloride and additional stirring was continued overnight at room temperature.

The reaction mixture was diluted with water and extracted with ethyl acetate.

The extract was washed with water, dried and the solvent was distilled off to give an oily substance. Thereafter, the oil was subjected to silica gel dry column chromatography to give 1.1 g. of crystalline product, which was recrystallized from benzene and cyclohexane to give the desired product as colorless crystals. m.p. 77°–79°C.

Analysis for C$_{14}$H$_{15}$NO$_2$: Calculated: C, 73.34; H, 6.59; N, 6.11. Found: C, 73.64; H, 6.75; N, 6.61.

IR spectrum (Nujol Mull, cm$^{-1}$): $\nu_{OH}$ 3311, 3165.
NMR spectrum ($\tau$, CDCl$_3$):
7.57 (3H, s, C$_2$—CH$_3$)
5.39 (2H, s, C$_5$—CH$_2$OH)

4.99 (2H, s, 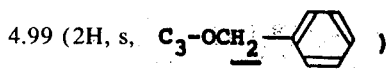 )

2.77 (1H, d, J=1.5, C$_4$—H)
2.10 (1H, d, J=1.5, C$_6$—H)

REFERENTIAL EXAMPLE 19

5-Methoxymethyl-2-methyl-3-pyridinol (No. 20)

2 G. of 5-bromomethyl-2-methyl-3-pyridinol was refluxed in 50 ml. of anhydrous methanol for 20 hours. The solvent was distilled off and the residue was poured on water, shaken with ethyl acetate and the ethyl acetate layer was discarded. The aqueous layer was neutralized with sodium bicarbonate and extracted with ethyl acetate.

The extract was washed with water, dried and the solvent was distilled off.

The resulting oil which crystallized gradually was recrystallized from ethanol-petrolium ether to give 0.82 g. of the desired product as colorless crystals. m.p. 134°–135°C.

Analysis for c$_8$H$_{11}$NO$_2$: Calculated: C, 62.72; H, 7.24; N, 9.14. Found: C, 62.58; H, 7.46; N, 8.95.

IR spectrum (Nujol Mull, cm$^{-1}$): $\nu_{OH}$ 2500.
NMR spectrum ($\tau$, (CD$_3$)$_2$SO):
7.64 (3H, s, C$_2$—CH$_3$)
6.73 (3H, s, C$_5$—CH$_2$OCH$_3$)
5.65 (2H, s, C$_5$—CH$_2$OCH$_3$)
2.9 (1H, d, J=2.0, C$_4$—H)
2.1 (1H, d, J=2.0, C$_6$—H)

Following the substantially same procedure as shown in referential example 19, the pyridinol derivative recited below was obtained:

5-Benzyloxymethyl-2-methyl-3-pyridinol (No. 21)

Colorless crystal, m.p. 135°–137°C

Analysis for C$_{14}$H$_{15}$NO$_2$: Calculated: C, 73.34; H, 6.59; N, 6.11. Found: C, 73.22; H, 6.61; N, 6.33.

The compounds of the formula (I) or the salts thereof are conveniently fed to poultry as a component of the feed or drinking water, but they may also be administered orally dispersed or admixed with other carriers.

According to one aspect of this invention, novel compositions are provided in which a pyridinol derivative or the salt thereof (I) is present as an active ingredient. Such compositions comprise the pyridinol derivative intimately dispersed in or admixed with an inert carrier. The term "inert carrier" as used herein means one that is substantially non-reactive with the active ingredient, orally ingestable and tolerated by the poultry.

The amount of pyridinol derivative required for control of coccidiosis in poultry will vary somewhat with the specific compound employed, the species of animals, the method or the object of application or with the symptons. Generally, the pyridinol derivatives (I) are effective in preventing the disease without undesirable side effect and toxic effect when administered at a level of more than about 0.005% by weight of the feed. For good prophylactic results, it is preferred that the feed contains between about 0.005 and 0.05% by weight of the active ingredient, more preferably between about 0.01 and 0.015%. When the pyridinol derivatives are to be employed for therapeutic purpose, the higher levels are used for shorter period of time. Thus, the concentrations of about 0.1 to about 0.2% by weight of the feed may be advantageously administered for treatment of coccidiosis. When these compounds are to be employed for therapeutic purpose, it is desirable to employ the lowest levels that exhibit anticoccidial activities, in order to eliminate any risk of said effects that may appear on prolonged feeding.

In preparing solid compositions, an uniform dispersion of the active ingredient throughout the carrier can be readily accomplished by the conventional methods of grinding, stirring or milling.

Many of these pyridinol derivatives of the salts thereof are advantageously administered to poultry by way of the drinking water of the birds. This method of treatment may often be employed in the therapeutic use, since poultry with coccidiosis are apt to consume less solid feed than normal birds. The water-soluble quaternary salts may be added directly to the drinking water.

According to another aspect of this invention, novel compositions are provided in which active ingredient is present in relatively large amounts and which are suitable for addition to the poultry feed directly or after intermediate dilution step. Such compositions which are a preferred feature of this invention are the so-called feed supplements or premix. Representative examples of the carriers to be employed in this invention are solid oral carriers such as distillers dried grains, corn starch, potato starch, fermentation residues, ground oyster shells, Attapulgus clay, rice bran, wheat bran, wheat middling, molasses soubles, corn meal, edible vegetable substances, soybean cake, soybean meal, antibiotic mycelis, crushed lime stone and the like. The quaternary salts are intimately dispersed or admixed throughout the solid inert carrier as described hereinabove. Formulations containing from about 5 to about 30 percent by weight, and preferably from about 10–25° by weight, of the active ingredient are particularly suitable for this purpose. It is preferable in the industry to use about 1–3 kg. of such a supplement per ton of feed.

Typical feed supplements containing pyridinol derivatives dispersed in an inert carrier include, for example, the following:

| quaternary salt | parts by weight |
|---|---|
| A. 5-hydroxymethyl-2-methyl-3-pyridinol | 25 |
| wheat bran | 75 |
| B. 5-hydroxymethyl-2-methyl-3-pyridinol hydrochloride | 20 |
| rice bran | 80 |
| C. 2-methyl-5-valeroyloxymethyl-3-pyridinol | 10 |
| soybean meal | 90 |

According to another aspect of this invention, the present composition may preferably include other known anticoccidial agents to broaden its anticoccidial spectrum and, sometimes, expect a synergistic effect.

Suitable examples of such anticoccidial agents include, for example, sulfa drugs, e.g., Sulfachloropyrazine, Sulfadimethoxine, Sulfaquinoxaline; thiamine derivatives, e.g., Beclotiamine, Amprolium, Dimethialium; quinoline derivatives, e.g., Buquinolate, Decoquinate, Methyl Benzoquate; folic acid antagonistic substances, e.g., pyrimethamin, Diaveridine; antibiotics, e.g., Monensin; Zolene (3,5-dinitro-o-toluamide), Clopidol (3,5-dichloro-2,6-dimethyl-4-pyridinol), Robenzidine; and the like.

The formulation of the compounds and the coccidiostatic activity of the compounds are more fully illustrated by the non-limiting examples as follows.

In these examples, all the parts are given by weight unless otherwise indicated.

EXAMPLE 1

Fifteen parts of 5-hydroxymethyl-2-methyl-3-pyridinol are uniformly mixed with 85 parts of wheat bran.

The resulting feed supplement contains 15% active ingredient. Uniform mixing of one part of the supplement with 1,000 parts of the poultry feed gives a feed composition containing 0.015% active ingredient.

EXAMPLE 2

Five parts of 5-hydroxymethyl-2-methyl-3-pyridinol and 5 parts of Sulfachloropyradine are uniformly mixed with 90 parts of rice bran.

The resulting feed supplement contains 10% active ingredients in total. One parts of the supplement is uniformly mixed with 10,000 parts of the poultry feed to give a feed containing 0.01% active ingredient in total.

EXAMPLE 3

The coccidiostatic activity of the pyridinol derivatives (I) or the salts thereof of this invention is determined by the following method:

Test Procedures

1. Chicks: Fourteen-day-old White Leghorn males (after hatched, fed a diet containing no anticoccidial agent and isolated as far as possible from the risk of extraneous coccidial infections) were used.
   Each group consisted of 10 chicks so as to avoid the difference of mean weight (significance level, 5%).
2. Infections: Each chick was inoculated orally into the crop with 100,000 sporulated oocysts of *Eimeria acervulina*.
3. Concentration of tested compouds: Each tested compound was mixed to the commercially available mixed feed at the concentration of 200 ppm.

After inoculation with oocysts, the chicks are fed a diet containing tested compounds for 6 days.

Control groups of infected or non-infected chicks are fed a similar diet which is free from coccidiostat.

They are weighed from the beginning of the test to the end, constantly. Daily oocyst outputs are determined as oocysts per gram feces during a period from day 4 to 6. The daily samples from each treatment are pooled and recorded as a percentage to that of the infected-unmedicated control.

At the end of this time, that is, 6 days after infection all chicks are sacrificed and the degree of the lesion of small intestines are indicated as a 0 to 4 visual scale and determined by the method of Johnson and Reid described in Experimental Parasitology vol. 28, 30–36 pp., (1970).

4. Explanation of findings set forth in Table 1 and 2:

$$\text{Relative rate of weight gain (\%)} = \frac{\text{Average weight gain of each group}}{\text{Average weight gain of uninfected-unmedicated group}} \times 100$$

The total of the weight gain from the begining of the test to the end devided with the number of the chicks is defined as "average weight gain".

Rate of oocyst production (%) = (Oocyst outputs of each) / (Oocyst outputs of infected unmedicated group) × 100

The accumulated oocyst outputs per gram feces during a period from day 4 to 6 is defined as "oocyst number".

Mean lesion score of intestine = (Total intestinal lesion of scores) / (Number of chicks)

The results are shown in Table 1.

Table 1

| Compound No. | | Rate of oocyst production (%) | Relative rate of weight gain (%) | Mean lesion score of intestine |
|---|---|---|---|---|
| 1 | | 0 | 95.5 | 0 |
| 1 | (hydrochloride) | 1.1 | 91.0 | 1.5 |
| 2 | | 0 | 95.0 | 0 |
| 3 | | 0 | 94.3 | 0 |
| 4 | | 0 | 94.1 | 0 |
| 9 | | 5.0 | 90.5 | 0.7 |
| 10 | | 2.8 | 92.4 | 0.5 |
| 17 | | 5.1 | 90.7 | 0.6 |
| 20 | | 3.9 | 83.9 | 1.6 |
| 21 | | 1.5 | 93.5 | 2.0 |
| 25 | (hydrochloride) | 0.1 | 100.0 | 0.3 |
| 29 | " | 1.1 | 89.3 | 1.6 |
| 30 | | 1.0 | 90.0 | 1.7 |
| 36 | (hydrochloride) | 0.3 | 102.0 | 0.8 |
| 38 | | 2.2 | 89.4 | 1.2 |
| 39 | | 0.6 | 103.0 | 0.6 |
| 40 | | 0.9 | 97.8 | 0.3 |
| 42 | | 0.3 | 97.8 | 1.0 |
| 49 | | 2.4 | 70.6 | 1.2 |
| 50 | | 1.8 | 90.4 | 1.0 |
| 52 | | 0.8 | 93.9 | 0.4 |
| 56 | | 2.0 | 81.0 | 1.9 |
| 57 | | 0 | 97.8 | 0 |
| 58 | | 0 | 94.4 | 0 |
| 60 | | 0 | 103.0 | 0 |
| 62 | | 0 | 101.5 | 0 |
| 66 | | 1.4 | 94.5 | 1.8 |
| 67 | | 0.5 | 97.9 | 0.6 |
| 68 | (hydrochloride) | 0.4 | 90.7 | 1.0 |
| 70 | | 0.9 | 91.3 | 0.8 |
| 78 | | 1.4 | 88.5 | 1.4 |
| 79 | | 1.4 | 84.6 | 0.6 |
| 86 | | 0 | 96.0 | 0 |
| 87 | | 4.0 | 90.0 | 0.9 |
| 91 | | 2.4 | 84.7 | 0.8 |
| 93 | | 2.7 | 70.4 | 1.2 |
| 101 | | 1.4 | 94.7 | 1.0 |
| 104 | | 0.9 | 96.0 | 1.0 |
| 105 | | 1.5 | 85.8 | 0.9 |
| 111 | | 4.5 | 90.0 | 0.9 |
| 116 | | 0.5 | 93.5 | 1.0 |
| 120 | | 2.2 | 72.5 | 1.6 |
| infected-unmedicated control | | 100 | 60.1 | 4.0 |
| uninfected-unmedicated control | | — | 100 | — |

It will be evident from the above results that the pyridinol derivatives of the abovementioned formula (I) or the salts thereof possess an extremely high degree of activity which cause coccidiosis, accompanying with good weight gain of the poultry without any unfavorable side effects.

It has also turned out that the coccidiostatic effect of the present composition was the highest at the first chizogony followed by the gametogony in various developmental stage of coccidia.

EXAMPLE 4

The coccidiostatic activity of the present compounds in combination with known anticoccidial agents was tested. The test procedure, chicks and coccidia used were substantially the same as shown in Example 3.

The results are shown in Table 2.

Table 2

| Compound tested | Conc. of active ingredient in feed (%) | Rate of oocyst production (%) | Relative rate of weight gain (%) | Mean lesion score of intestine |
|---|---|---|---|---|
| 2-methyl-5-hydroxy-3-pyridinol | 0.005 | | | |
| + | + | 3.0 | 95.0 | 0.8 |
| Beclotiamine hydrochloride | 0.01 | | | |
| 2-methyl-5-hydroxy-3-pyridinol | 0.005 | | | |
| + | + | 0.5 | 97.0 | 0.1 |
| Sulfachloropyrazine | 0.01 | | | |
| 2-methyl-5-hydroxy-3-pyridinol | 0.005 | 13.0 | 82.3 | 2.0 |
| Beclotiamine hydrochloride | 0.01 | 31.0 | 78.5 | 2.4 |
| Sulfachloropyrazine | 0.005 | 21.5 | 82.0 | 2.1 |
| Infected-unmedicated control | — | 100 | 59.3 | 4.0 |
| Uninfected-unmedicated control | — | — | 100 | — |

What is claimed is:

1. An anticoccidial composition which comprises a compound of the formula

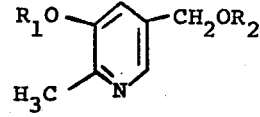

intimately dispersed in an inert edible carrier, wherein $R_1$ and $R_2$ are each hydrogen or a phosphono group, and at least $R_1$ or $R_2$ is said phosphono group; or a salt thereof.

2. The composition of claim 1, wherein the compound is 2-methyl-5-phosphonoxymethyl-3-pyridinol.

3. The composition of 1, wherein said salt is an acid adduct salt of said compound and an acid selected from the group consisting of hydrochloric, sulfuric, nitric, phosphonic, acetic, propionic, lactic, oxalic, succinic, maleic, tartaric, citric, benzoic, phthalic, terephthalic and naphthalene sulfonic acid.

4. The poultry feed having dispersed therein for control of poultry coccidiosis at least about 0.005% by weight of a compound of the formula

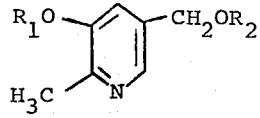

wherein R₁ and R₂ are each hydrogen or a phosphono group, and at least R₁ or R₂ is said phosphono group; or a salt thereof.

5. The poultry feed of claim 4, wherein the compound is 2-methyl-5-phosphonoxymethyl-3-pyridinol.

6. A poultry feed of claim 4, wherein said salt is an acid adduct salt of said compound and an acid selected from the group consisting of hydrochloric, sulfuric, nitric, phosphonic, acetic, propionic, lactic, oxalic, succinic, maleic, tartaric, citric, benzoic, phthalic, terephthalic and naphthalene sulfonic acid.

7. A method of controlling poultry coccidiosis which comprises orally administering to poultry susceptible to coccidiosis an anticoccidial amount of a compound of the formula

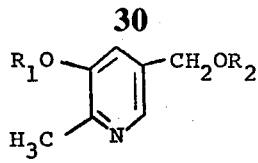

wherein R₁ and R₂ are each hydrogen or a phosphono group, and at least R₁ or R₂ is said phosphono group; or a salt thereof.

8. The method of claim 7, wherein the compound is 2-methyl-5-phosphonoxymethyl-3-pyridinol.

9. The method of claim 7, wherein said salt is an acid adduct salt of said compound and an acid selected from the group consisting of hydrochloric, sulfuric, nitric, phosphonic, acetic, propionic, lactic, oxalic, succinic, maleic, tartaric, citric, benzoic, phthalic, terephthalic and naphthalene sulfonic acid.

* * * * *

UNITED STATES PATENT OFFICE
CERTIFICATE OF CORRECTION

PATENT NO. : 3,935,311
DATED : January 27, 1976
INVENTOR(S) : YASUHIRO MORISAWA et al It is certified that error appears in the above-identified patent and that said Letters Patent are hereby corrected as shown below:

Cover page, at "[45]" - replace "Jan. 27, 1975" with
--- Jan. 27, 1976 ---.

Column 1, line 37 - replace "there" with --- their ---.

Column 2, line 16 - replace "posses" with --- possess ---.

Column 2, line 22 - replace "parctically" with
--- practically ---.

Column 2, line 52 - replace "2-thermoyl" with
--- 2-thenoyl ---.

Column 7, line 6 - replace "aklali" with --- alkali ---.

Column 11, line 50 - before "103", replace "Nos." with
--- No. ---.

Column 13, line 3 - replace "5,56" with --- 5.56 ---.

Column 15, line 5 - replace "73,16" with --- 73.16 ---.

Column 15, line 16 - replace "-3-methyl-3-(-phenoxy-" with
--- -3-(α-phenoxy- ---.

Column 24, line 9 - replace "2 G." with --- 2 g. ---.

UNITED STATES PATENT OFFICE
CERTIFICATE OF CORRECTION

PATENT NO. : 3,935,311
DATED : January 27, 1976
INVENTOR(S) : YASUHIRO MORISAWA et al It is certified that error appears in the above-identified patent and that said Letters Patent are hereby corrected as shown below:

Column 24, line 22 - replace "$c_8H_{11}NO_2$" with --- $C_8H_{11}NO_2$ ---.

Column 25, line 9 - replace "of" with --- or ---.

Signed and Sealed this eighteenth Day of May 1976

[SEAL]

Attest:

RUTH C. MASON
Attesting Officer

C. MARSHALL DANN
Commissioner of Patents and Trademarks